US011135188B2

(12) United States Patent
First et al.

(10) Patent No.: US 11,135,188 B2
(45) Date of Patent: Oct. 5, 2021

(54) METHOD AND COMPOSITION TO IMPROVE ABSORPTION OF THERAPEUTIC AGENTS

(75) Inventors: Eric R. First, Morristown, NJ (US); Ashish B. Patel, West Orange, NJ (US); Guido Schmitz, Sparta, NJ (US); Stephanie Petaway-Hickson, Morris Plains, NJ (US); Hung-Huar Tong, Basking Ridge, NJ (US)

(73) Assignee: Bayer HealthCare LLC, Whippany, NJ (US)

( * ) Notice: Subject to any disclaimer, the term of this patent is extended or adjusted under 35 U.S.C. 154(b) by 1081 days.

(21) Appl. No.: 12/387,977

(22) Filed: May 11, 2009

(65) Prior Publication Data

US 2010/0286100 A1 Nov. 11, 2010

(51) Int. Cl.
  *A61K 31/192* (2006.01)
  *A61K 9/20* (2006.01)
  *A61K 31/167* (2006.01)
  *A61K 9/14* (2006.01)

(52) U.S. Cl.
  CPC ............ *A61K 31/192* (2013.01); *A61K 9/143* (2013.01); *A61K 9/2009* (2013.01); *A61K 31/167* (2013.01)

(58) Field of Classification Search
  None
  See application file for complete search history.

(56) References Cited

U.S. PATENT DOCUMENTS

| | | | |
|---|---|---|---|
| 2,293,359 | A | 8/1942 | Quisling |
| 5,665,388 | A | 9/1997 | Phykitt |
| 6,284,269 | B1 | 9/2001 | Struengmann et al. |
| 2003/0180352 | A1* | 9/2003 | Patel .................. A61K 9/1617 424/465 |
| 2005/0147668 | A1* | 7/2005 | Bertelsen ............ A61K 9/1611 424/464 |
| 2006/0105039 | A1* | 5/2006 | Lai et al. ....................... 424/470 |
| 2007/0141144 | A1 | 6/2007 | Roberts et al. |
| 2007/0218128 | A1* | 9/2007 | Bertelsen ............... A61K 9/143 424/464 |
| 2009/0311327 | A1 | 12/2009 | Roberts et al. |

FOREIGN PATENT DOCUMENTS

| | | |
|---|---|---|
| EP | 0414688 B1 | 8/1994 |
| GB | 191225486 A | 4/1913 |
| RU | 2099058 C1 | 12/1997 |
| RU | 2170582 C1 | 7/2001 |
| WO | 2005105102 A1 | 11/2005 |
| WO | 2010132095 A1 | 11/2010 |

OTHER PUBLICATIONS

Bosch, William H.; "Pharmaceutical Applications of Finely Dispersed Systems," from "Medicinal Applications of Colloids" (Egon Mtijevic ed.), 2008, Springer, pp. 69-93.*
Horn, Dieter and Reiger, Hans; "Organic Nanoparticles in the Aqueous Phase—Theory, Experiment, and Use," Wiley-Vch, 2001, Angew. Chem. Int. Ed., vol. 40, pp. 4330-4361.*
Liversidege, Gary G. and Elaine M.; "Drug Nanoparticles: Formulating Poorly Water-Soluble Compounds," SAGE, 2008, Toxicologic Pathology, vol. 36, pp. 43-48.*
Horter, D; and Dressman, J.B.; "Influence of physicochemical properties on dissolution of drugs in the gastrointestinal tract," Elsevier, 2001, Advanced Drug Delivery Reviews, vol. 46, pp. 75-87.*
Date, Abhijit A.; and Patravale, V.B.; "Current Strategies for engineering drug nanoparticles," Elsevier, 2004, Current Opinion in Colloid & Interface Science, vol. 9, pp. 222-235.*
Ely, Leticia et al.; "Effervescent dry powders for respiratory drug delivery," 2007, Elsevier; European Journal of Pharmaceutics and Biopharmaceutics, vol. 65, pp. 346-353.*
Ansel, Howard C., et al.; "Pharmaceutical Dosage Forms and Drug Delivery Systems," 7th ed.; 1999; Lippincott, Williams and Wilkins; p. 38.*
Orton, D., et al.; "Plasma salicylate levels after soluble and effervescent aspirin." 1979, British journal of clinical pharmacology 7, No. 4, pp. 410-412.*
Nicolic, Lovorka et al.; "Influence of In Vitro Test Conditions on Release of Aspirin from Commercial Tablets," 1992; American Pharmaceutical Assn.; Journal of Pharmaceutical Sciences, vol. 81, No. 4, pp. 386-391.*
Orton, D., et al.; "Plasma salicylate levels after soluble and effervescent aspirin." 1979, British journal of clinical pharmacology 7, No. 4, pp. 410-412. (Year: 1979).*
Nicolic, Lovorka et al.; "Influence of In Vitro Test Conditions on Release of Aspirin from Commercial Tablets," 1992; American Pharmaceutical Assn.; Journal of Pharmaceutical Sciences, vol. 81, No. 4, pp. 386-391. (Year: 1992).*
"Extended European Search Report for Application No. EP10775187.7 dated Sep. 25, 2012".
"International Search Report for Application No. PCT/US2010/001375 dated Jul. 1, 2010".
Remington; et al., "Pharmaceutical Sciences, 18th Edition", Mack Publishing Company, Easton, Pennsylvania, 1990, 592-593.
Javaid; et al., "Dissolution of Aspirin from Tablets Containing Various Buffering Agents", Journal of Pharmaceutical Sciences, Oct. 1, 1972, vol. 61 No. 9, 1370-1373.

* cited by examiner

*Primary Examiner* — David J Blanchard
*Assistant Examiner* — Ivan A Greene

(57) ABSTRACT

A tablet with an enhanced dissolution profile for a medicinally active ingredient such as aspirin and methods for making the tablet. The tablet comprises a blend of crystals of the medicinally active ingredient and a dissolution aid such as sodium or calcium carbonate or bicarbonate that coats the crystals upon co-milling. The blend is then compressed to form tablets that have an enhanced dissolution profile for the medicinally active ingredient.

3 Claims, 7 Drawing Sheets

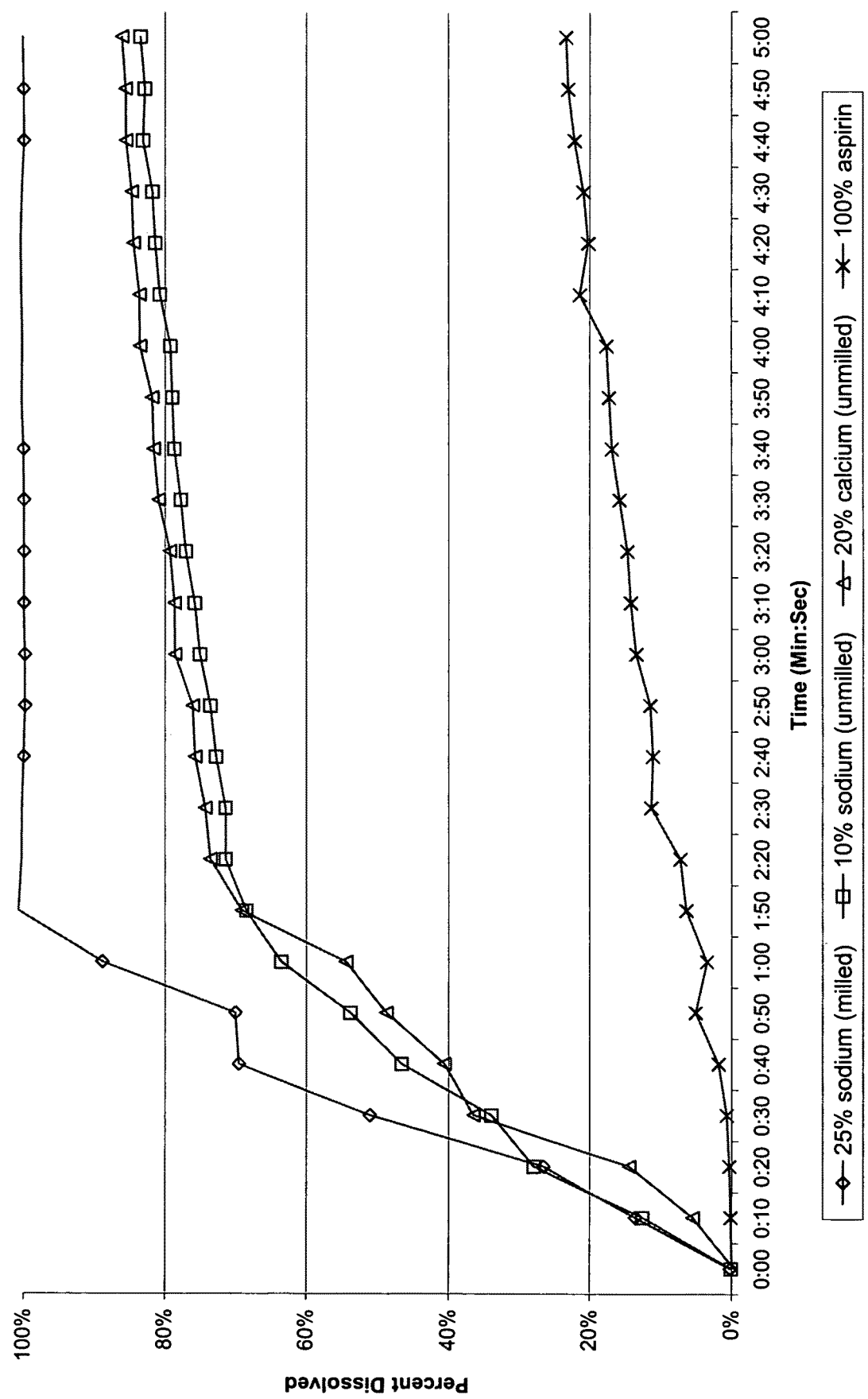

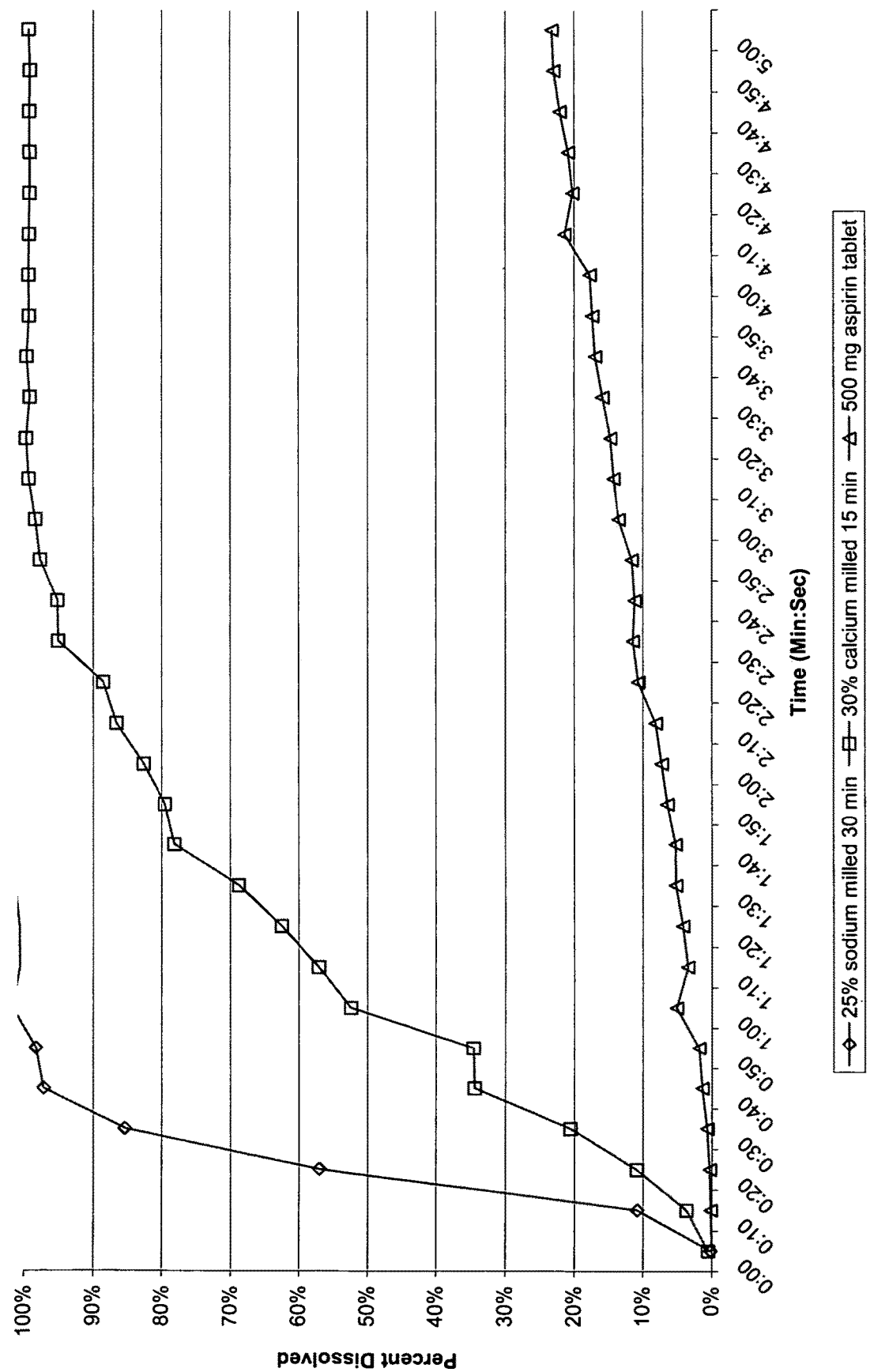
Figure 5 - Average Dissolution Rates

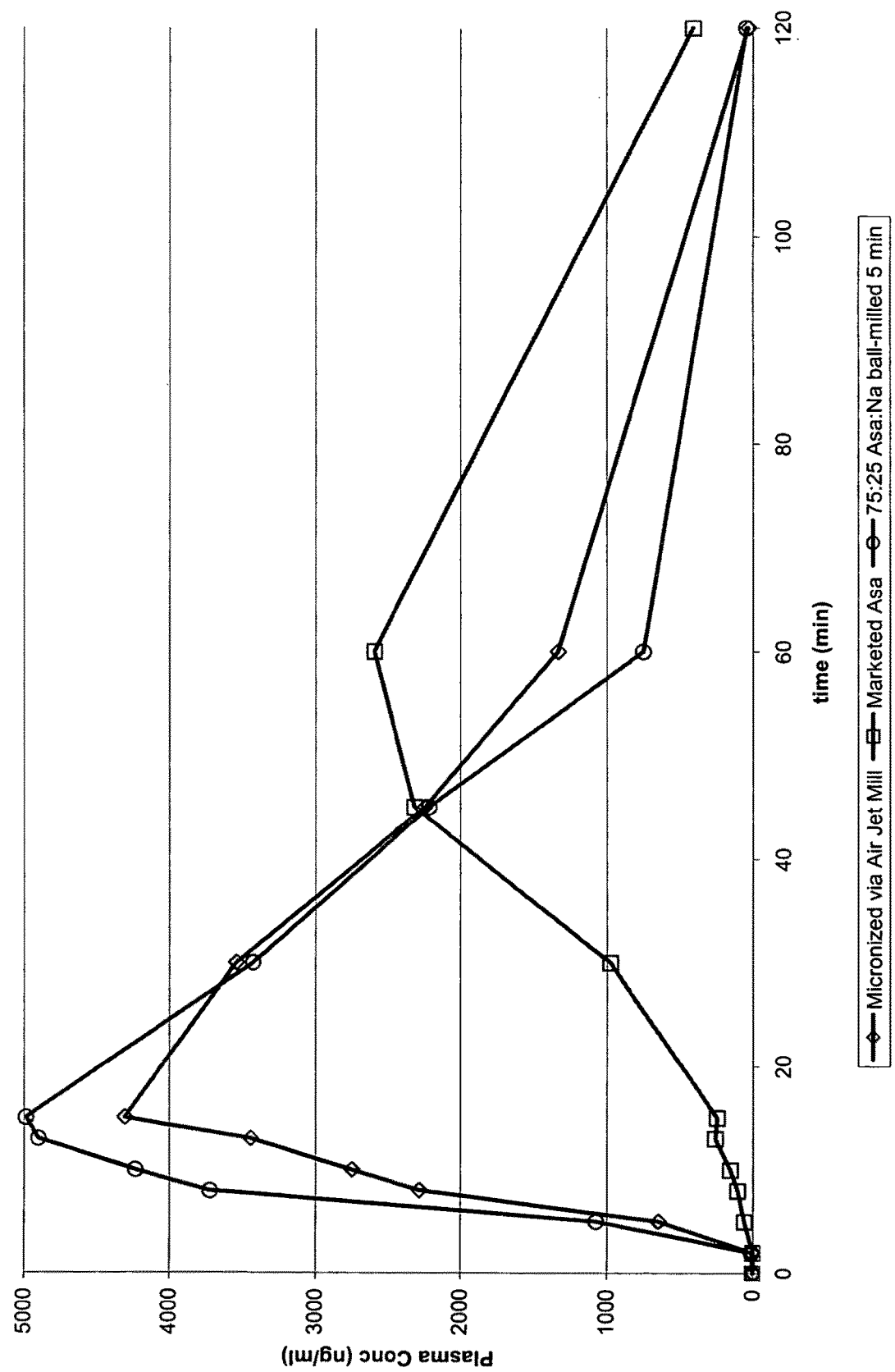

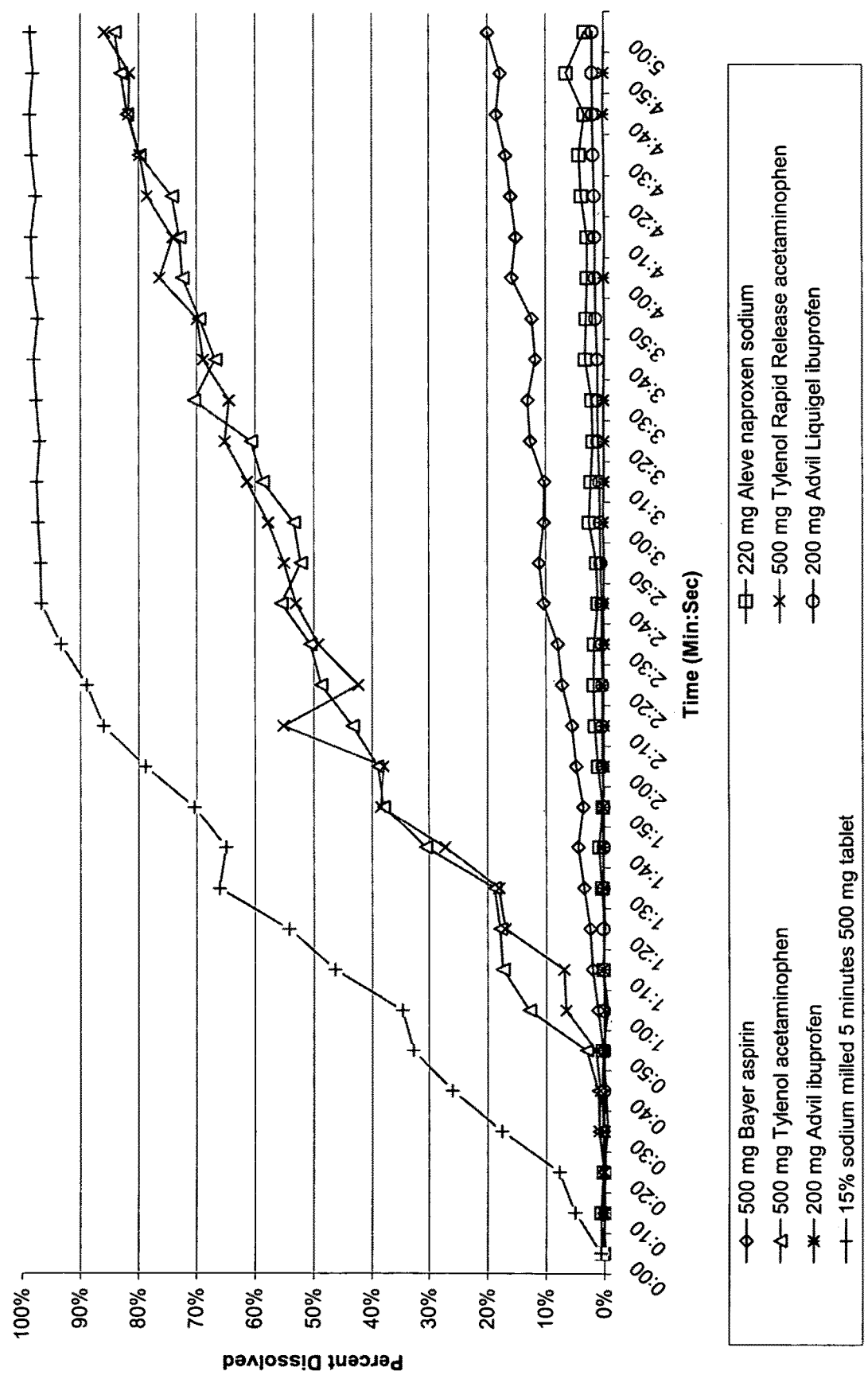

METHOD AND COMPOSITION TO IMPROVE ABSORPTION OF THERAPEUTIC AGENTS

FIELD OF THE INVENTION

The invention relates to a composition and method to improve absorption and gastrointestinal tolerability for therapeutic drugs, especially aspirin. The composition may be incorporated into solid dosage forms such as a pharmaceutical tablet.

BACKGROUND OF THE INVENTION

Solid dosage forms, such as capsules, tablets and caplets, are very popular delivery mechanisms for doses of medicinal compounds. These forms generally provide a reliable dosage amount and are suitable for mass production. Unlike injections, solid dosage forms do not require medical expertise for administration, so patients may take the medicine at home.

Unlike injections and other direct administration techniques that deliver the medicinal compound directly to the bloodstream, solid dosage forms such as tablets must be absorbed into the bloodstream through the gastrointestinal tract. This difference presents both advantages and disadvantages for solid dosage forms.

One advantage of solid dosage forms is that, through various coatings and manufacturing techniques, solid dosage forms can be designed to be absorbed in various parts of the gastrointestinal tract. Enteric coatings and sustained release technologies allow for delayed absorption of the medicinal compound and may allow a single dose of one or two tablets to provide a medicinal effect throughout the day.

One disadvantage of solid dosage forms, when compared to injections and other direct administration techniques, is that solid dosage forms do not provide immediate medicinal benefits. Tablets and other solid dosage forms take time to be absorbed into the bloodstream. For some medicinal ingredients, such as analgesics, that are ingested in response to a perceived problem, such as a headache, the delay of onset of relief can be frustrating for a patient.

Another disadvantage of solid dosage forms is that some medicinal ingredients may not be well tolerated by the stomach or intestines. For example, non-steroidal anti-inflammatory drugs ("NSAIDs") that are used as analgesics can have undesired effects on the stomach. The label for Advil® brand ibuprofen, for example, warns that the product may cause stomach bleeding.

Since solid dosage forms are so popular and so convenient, many different approaches have been tried to overcome some of these disadvantages.

One approach to solving the delayed onset of action problem has been to abandon tablets in favor of liquids or powders. For over-the-counter analgesics, for example, effervescent tablets that dissolve in a glass of water or powders carried in individual envelopes have been tried. While these approaches have overcome some disadvantages of tablets and solid dosage forms, these approaches have drawbacks of their own. Effervescent tablets tend to be significantly larger than tablets that are to be swallowed directly, and so can be less durable and portable than smaller tablets. Powders generally do not taste very good, and the large surface area of a powder, when compared to a compressed tablet, at least, can ensure an unpleasant taste experience for the patient.

Various quick-dissolve technologies have also been tried. These technologies generally provide for a tablet that dissolves quickly on the tongue, allowing for ease of administration and quick onset of action. But, these technologies can suffer from the same problems found with effervescent tablets and powders. Quick-dissolve tablets are generally larger and not as highly compressed as tablets, so they are not as durable as compressed tablets, and, if the medicinal ingredient has a bad taste, the bad taste can still be detected while the quick-dissolve tablet is being swallowed.

Other approaches include various coating techniques that allow the tablet to pass through the stomach undissolved, but delay the onset of action, and various soft gel and liquid gel approaches that enrobe liquid medicines in gelatin coatings. If the gelatin coating on these soft gels is too thick, however, the soft gel may not dissolve quickly, but if the gelatin coating is too thin, the soft gel may leak or may not be sufficiently durable for the demands of large scale manufacturing and distribution.

The search continues for a solid dosage form, particularly a compressed tablet, that retains all the benefits of solid dosage forms, but that also has increased absorption in the stomach to speed the onset of medicinal effect and to limit the possibility of unpleasant interaction with the stomach for medicinal compounds that may have such an unpleasant interaction.

One promising avenue of investigation is reducing the particle size of the medicinal ingredient in the tablet. Due to surface area effects, smaller particle sizes, theoretically, should improve solubility, particularly for less soluble materials. In general there is a correlation between reducing particle size and dissolution rate; the smaller the size the faster the dissolution profile.

Various micronization or submicronization techniques are known, in which medicinal compounds are milled to about a 1-10 micron size range. These techniques include air/jet, ball and pin milling techniques. Other techniques have been used to reduce particles to a size from less than about one micron down to about 100 nanometers. These techniques are generally propriety milling or high pressure homogenization technologies. These techniques, however, are not generally useful for medicinal products, particularly in the over-the-counter field. High costs associated with producing a smaller particle and higher instability of some medicinal compounds, such as aspirin, can become very unstable at these lower particle sizes; aspirin becomes unstable in micronization methods that are fluid based.

One example of a technique to reduce particle size is Elan's NanoCrystal® technology. That technology, discussed on Elan's website, reduces particle size to less than about 2,000 nanometers using a proprietary wet-milling technique. The particles are stabilized against agglomeration by surface adsorption of selected stabilizers. The particles can be used to form a colloidal dispersion in water that is claimed to behave like a true aqueous solution. Particle sizes for naproxen for example, have been reduced to about 250 nanometers.

Another approach to improving solubility is to add materials to tablets that increase the rate at which the tablets disintegrate in the stomach or intestine. These ingredients can include effervescent materials, even though most popular effervescent products are dissolved in liquids outside the body to reduce the problems inherent in evolution of gas. Other tablet disintegrants are well known and include starch, starch glycolates, crosslinked polyvinyl pyrrolidone, alginates, cellulose materials including methyl cellulose, crosslinked sodium carboxymethyl cellulose, and microcrystalline cellulose, some ion exchange resin materials, gums, such a guar gum, Gellan gum, and gum Karaya, chitin and chitosan, agar, polacrillin potassium, and Isapghula husks. These materials are generally added to the tablet blend before compression to aid in the disintegration of the tablet upon ingestion.

Starch has been known as a disintegrant for many years. Its ability to aid in tablet disintegration has been attributed both to better and more thorough disintegration of the tablet and to a suggested surface layer of fine starch particles on hydrophobic drug crystals that impart a hydrophilic property to the granular formation thereby increasing the effective surface area of the crystals. (Remington's Pharmaceutical Sciences, 18$^{th}$ Edition, pp. 592-93 (1990).) The same source also reported that phenobarbital granulated with gelatin solution (presumably a wet granulation process) dissolved faster than those granulated with sodium carboxymethylcellulose or polyethylene glycol 600 as a binder.

One technique for increasing the absorption rate of medicinal agents is found in European Patent Publication No. 414,688 to Neuvonen. In this patent, the dissolution rate of a medicinal agent that is either too slow or too rapid for its intended application is regulated by addition of a magnesium, aluminum, or sodium dissolution aid. Suitable medicinal agents include carboxylic acid derivatives such as anthranil acid derivatives, propionic acid derivatives, acetic acid derivatives salicylic acid derivatives (and salts of these acid derivatives) and pyrazolone or benzothiazone derivatives. Acceptable dissolution aids include magnesium hydroxide, magnesium oxide, aluminum oxide and sodium carbonate or bicarbonate or mixtures thereof. The presence of aluminum oxide was reported to slow solubility. The formulations could be made into tablets, capsules or powders. Tablets were made by mixing the medicinal ingredient and the dissolution aid, corn starch, lactose (or sodium bicarbonate), and microcrystalline cellulose in a dry blender, moisturizing and granulating with an aqueous or water-in-ethanol solution of polydidone. The dried granules were sieved, magnesium stearate was added and the resulting mixture was compressed into tablets. Powders and capsules were formed by mixing the ingredients without compression and putting the mixed ingredients into capsules or into packages for use as a powder.

Despite these techniques, the search continues for inexpensive, reliable techniques to increase the dissolution profile of medicinal materials that do not suffer from the disadvantages of the existing art.

SUMMARY OF THE INVENTION

The principal object of the invention therefore is to provide a technique for increasing the solubility of medicinal compounds in tablet form to decrease residence time in the stomach (or small intestine for enteric tablets).

Another object of the invention is to provide a physical form of material containing a medicinal compound with a reduced residence time in the stomach or small intestine.

Another object of the present invention is to provide a milled NSAID selected from the group consisting of acetaminophen, ibuprofen, naproxen and ketoprofen and salts thereof, milled in combination with a solubility aid that has an improved dissolution profile when compared to an NSAID that has not been milled with a solubility aid.

Another object of the present invention is to provide therapeutic combinations having enhanced solubility comprising NSAIDs in combination with one or more medicinal agents such as: (a) sympathomimetic amine drugs, such as decongestants including pseudoephedrine, phenylephrine, and phenylpropanolamine; (b) beta blockers such as ranitidine, famotidine, cimetidine and nizatidine; (c) anti-histamines such as diphenhydramine hydrochloride, brompheniramine, chlorpheniramine, dimenhydrinate, diphenhydramine, and doxylamine or piperazine derivatives chosen from the group consisting of; ceterazine hydrochloride and meclizine, and loratadine; (d) calcium channel blockers such as bepridil (Vasocor), diltiazem (Cardizem), and verapamil (Isoptin, Calan); (e) nutritional supplements such as co-Q10, ginseng, lycopene, glucosamine/chondroitin, S-adenosylmethione, curcumin, holy basil, zinc, omega 3 fatty acids DHA and EPA, Vitamin C, Vitamin E; (f) Cox-II inhibitors including Celecoxib; and (g) selective serotonin re-uptake inhibitors (SSRIs) such as fluoxetine (PROZAC), sertraline (ZOLOFT), paroxetine (PAXIL™), fluvoxamine (LUVOX), citalopram (CELEXA) and escitalopram (LEXAPRO).

An advantage of the invention is that it can provide pharmaceutical, particularly analgesic, tablets having good workability and a fast dissolution rate that provides an enhanced onset of therapeutic benefit, such as pain relief, with less gastrointestinal irritation.

To achieve the foregoing objects and in accordance with the purpose of the invention, as embodied and broadly described herein, the invention provides a method for manufacturing a pharmaceutical tablet comprising the steps of: preparing a pre-blend of crystals of a medicinally active ingredient and a dissolution aid; milling the pre-blend for a time sufficient to establish a particle size of the crystals of not more than about 40 μm and to substantially coat said crystals with the dissolution aid to form a blend; and compressing the blend into a tablet shape.

The invention further provides a micronized combination of a medicinal ingredient, such as aspirin, and a dissolution aid, such as an alkaline carbonate, that, when combined in a pre-determined ratio to form an alkaline protective coating, forms a free flowing powdered formulation for forming a tablet.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

BRIEF DESCRIPTION OF THE DRAWINGS

FIG. 4 depicts the first five minutes of the average dissolution curves for various formulations of aspirin and carbonates made as set forth in Example 8 and Table 10. These formulations contained excipients and did not undergo roller-compaction.

FIG. 5 (Graph 2) depicts the dissolution curves for various formulations of aspirin and carbonates made in accordance with the invention. These formulations contained excipients and did not undergo roller-compaction.

FIG. 6 (Graph 3) depicts in-vivo PK data in dogs. The date compares 500 mg Bayer® aspirin and two formulations: aspirin micronized via airjet mill and aspirin and sodium carbonate milled vial ball mill.

FIG. 7 (Graph 4) depicts an in-vitro dissolution comparison of the claimed invention compared to several commercial products: Advil® 200 mg liquid gels, Tylenol® 500 mg rapid release capsules, and Bayer® 500 mg aspirin.

DETAILED DESCRIPTION OF THE PREFERRED EMBODIMENTS

Figure 1:
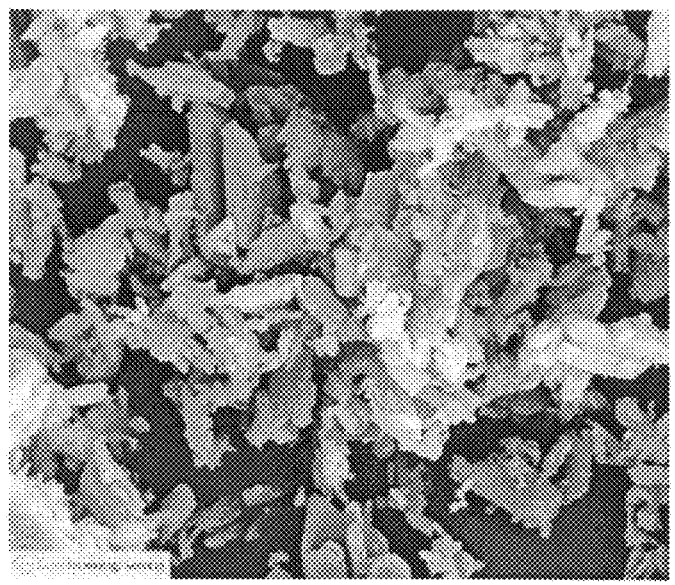
FIG. 1 depicts aspirin particles that have been milled to a reduced particle size shown at 283 times magnification.

Reference will now be made in detail to the presently preferred embodiments of the invention.

Many pharmaceutical tablets are manufactured in a similar manner: the active ingredient is subjected to a wet or dry granulation process to prepare particles of the active having a desired size, the active material is then combined with other ingredients useful in tablet manufacturing, and the resulting mixture is then compressed into tablets for administration to patients.

Certain materials, such as aspirin, are very sensitive to environmental conditions such as moisture or heat, or both. As a result, these materials may only be treated with non-water based milling methods such as dry milling, ball milling, and bead milling.

Most efforts to alter the dissolution profile of medicinally active materials have focused either on the milling process, by grinding the active crystals to ever smaller sizes, or on addition of various materials to the final mixture that is compressed into tablets.

Tablets in accordance with the invention are made through a different process. A medicinally active compound is co-milled with a dissolution aid for a period of time sufficient to form a dissolvable matrix. This matrix contains both crystals of the medicinally active compound and the dissolution aid. This co-milled matrix is then combined with other ingredients to form a mixture that is then formed into tablets.

Without being bound to a particular theory of the invention, it appears that co-milling of a medicinal ingredient, especially a soluble active ingredient such as aspirin together with a dissolution aid such as a carbonate, such as sodium carbonate for a determined amount of time leads to the carbonate enveloping the aspirin particles thereby protecting them from moisture. This envelopment combined with the smaller particle size of the ingredients, leads to an unexpected, synergistic improvement in the dissolution profile for the medicinally active ingredient. The improvement in dissolution rate of the formulation leads to a faster absorption profile and improvement in the pharmacokinetic profile of the medicinal ingredient.

Moreover, when the milling step is followed directly by roller compaction of the co-milled ingredients, the tablet does not require additional excipients e.g., fillers, binders, and/or stabilizers. Without being bound by a theory of the invention, this surprising advantage appears to stem from the combination of a reduction in particle size and from the intimacy of the contact between the medicinal ingredient and the dissolution aid, which appears to cause the dissolution aid to act like a starch or binder, thereby removing the need for a separate filler.

These advantages are obtained despite the fact that the medicinally active ingredient has not been co-milled to the smallest possible particle size. Instead, a certain optimal time of milling appears to provide the advantages of the invention without requiring extensive milling or specialized equipment.

In accordance with the invention, a medicinal ingredient is first selected for use. The selection of the medicinal ingredient will affect almost all of the other parameters of the blend and tablet. If the medicinal ingredient is very durable and sturdy, less stringent limits are placed on additional materials and processes. More sensitive medicinal ingredients will require more particular requirements for additional materials and processes. Acceptable medicinal ingredients include, but are not limited to, analgesics, such as acetaminophen, aspirin and non-steroidal anti-inflammatory drugs (NSAIDs) such as ibuprofen, ketoprofen, naproxen and salts thereof, such as naproxen sodium; sympathomimetic amine drugs such as decongestants including pseudoephedrine, phenylephrine, and phenylpropanolamine; histamine $H^2$-receptor antagonists such as ranitidine, famotidine, cimetidine and nizatidine; anti-histamines such as diphenhydramine hydrochloride, brompheniramine, chlorpheniramine, dimenhydrinate, diphenhydramine, and doxylamine or piperazine derivatives chosen from the group consisting of; ceterazine hydrochloride and meclizine, and loratadine; beta blockers such as cartelol (carteolol hydrochloride), propafenose hydrochloride (RYTHMOL SR®), pindolol (VISKEN®), rimipril (ALTACE®), atenolol (TENORMIN®); calcium channel blockers such as bepridil (VASOCOR®), diltiazem (CARDIZEM®), and verapamil (ISOPTIN®, CALAN®); nutritional supplements such as co-Q10, ginseng, lycopene, glucosamine/chondroitin, S-adenosylmethione, curcumin, holy basil, zinc, omega 3 fatty acids DHA and EPA, Vitamin C, Vitamin E, Saint John's Wort; Cox-II inhibitors including Celecoxib (CELEBREX®), valdecoxib (BEXTRA®); muscle relaxant medicinal ingredients alone or in combination with an NSAID or analgesic such as carisoprodol and aspirin, methocarbamol and aspirin (ROBAXIN®) cyclobenzaprine HCl (FLEXERIL®), benzodiazepines such as clonazepam (KLONOPIN®), diazepam (VALIUM®); alprazolanm (XANAX®); codeine and synthetic derivatives alone or in combination with an analgesic such as hydrocodone, oxyocodone and acetaminophen (TYLOX®), Hydrocodone Bitartrate and Acetaminophen (VICODIN®), Oxycodone Hydrochloride (ROXICODONE®), Acetaminophen and Codeine; selective serotonin re-uptake inhibitors (SSRIs) such as fluoxetine (PROZAC®), sertraline (ZOLOFT®), paroxetine (PAXIL®), fluvoxamine (LUVOX®), citalopram (CELEXA®) and escitalopram (LEXAPRO®), and combinations thereof. Preferred medicinal ingredients include analgesics, such as acetaminophen, aspirin, and other NSAIDs such as ibuprofen, ketoprofen and naproxen and salts thereof, either alone or in combination with other medicinal ingredients. Highly preferred medicinal ingredients include aspirin and naproxen sodium, either alone or in combination with other medicinal ingredients as listed above.

The medicinal ingredient is then combined with a dissolution aid to form a pre-blend. Acceptable dissolution aids include alkali; salts in the form of sodium, calcium, magnesium and potassium carbonates and bicarbonates and glycinates; tribasic sodium and potassium phosphates and mixtures thereof; other agents such as gaseous agents that produce a gas for example nitric oxide, and hydrogen sulfide which aid in the dissolution process whereas the gas or bubbles promote dissolution. Preferred dissolution aids include sodium carbonate, sodium bicarbonate, calcium carbonate, and calcium bicarbonate, including soda ash and calcined soda. Highly preferred dissolution aids include sodium carbonate and calcium carbonate.

The optimal ratio of the weight percent of dissolution aid and medicinally active ingredient and the proper type of dissolution aid should be considered when preparing a tablet in accordance with the invention. A greater proportion of dissolution aid can improve the dissolution rate, but, depending on the medicinally active ingredient and the dissolution aid chosen, may reduce stability of the medicinally active ingredient. Lower proportions of the dissolution aid may not improve dissolution sufficiently. The wrong dissolution aid may chemically destabilize the medicinally active ingredient.

Preferably, tablets in accordance with the invention comprise a therapeutic amount of the medicinally active ingredient, for example from about 37 mg. to about 500 mg aspirin, and an effective amount of a dissolution aid, for example sodium or calcium carbonate in an amount from about 5% to about 40% of the amount of aspirin present in the tablet. More preferably, the pre-blend of materials should comprise at least about 10% by weight of the dissolution aid, more preferably at least about 20% by weight, and most preferably at least about 25% by weight of the dissolution aid.

The pre-blend of the medicinal ingredient and the dissolution aid is milled. The preferred milling technique can be selected by one skilled in the art based on the stability of the medicinal ingredient and the desired particle size. Dry milling techniques include ball milling, air-jet milling, and spray drying. These techniques may be used with materials such as aspirin, but spray drying does not generally provide particles of a sufficiently small size, so ball milling and air-jet milling are preferred. Wet milling techniques include precipitation, bead milling (wet), and super-critical $CO_2$ treatment. Super-Critical $CO_2$ milling is not compatible with aspirin due to the exposure to moisture during the process, and wet milling techniques in general are not preferred with medicinal ingredients that are more susceptible to degradation in liquid environments. Moreover, wet milling generally requires an additional process step, such as spray drying, to remove the liquid from the milled material before further processing.

It is possible with some medicinal ingredients to avoid milling entirely using direct crystal synthesis techniques such as crystal synthesis and various precipitation methods. These techniques, however, are not appropriate with active ingredients that do not tolerate water well, and such techniques also do not appear to provide the benefits of the invention. Moreover, the resulting crystals must still be milled with a dissolution agent to gain the benefit of the invention.

The blend should be milled to reach an average particle size for the medicinal ingredient of less than about 50 μm. More preferably, the blend should be milled to reach an average particle size of less than about 40 μm, and most preferably to a size of less than about 10 μm measured by a scanning electron microscopy (SEM) using laser diffraction on a MS 2000 Hydro S machine.

The milling time should be sufficient to impart the coating effect of the dissolution aid on the blend. This time should not generally be less than about three minutes to achieve the benefits of the invention, and more preferably not less than about 5 minutes and most preferably not less than about 10 minutes. The milling time should not extend too long, however. Too great a reduction in particle size can impact stability of the medicinally active ingredient and result in agglomeration of crystals. Moreover, heat is generated with increasing milling time, which can affect the stability of certain medicinally active ingredients. Thus, the milling time cannot be too short, because the particles will not be reduced to a small enough size, but neither can the milling time be too long, lest the stability of the medicinally active ingredient be affected. Thus, the maximum time for milling should not be more than about sixty minutes, preferably not more than about forty five minutes and most preferably not more than about thirty minutes.

Figure 2:
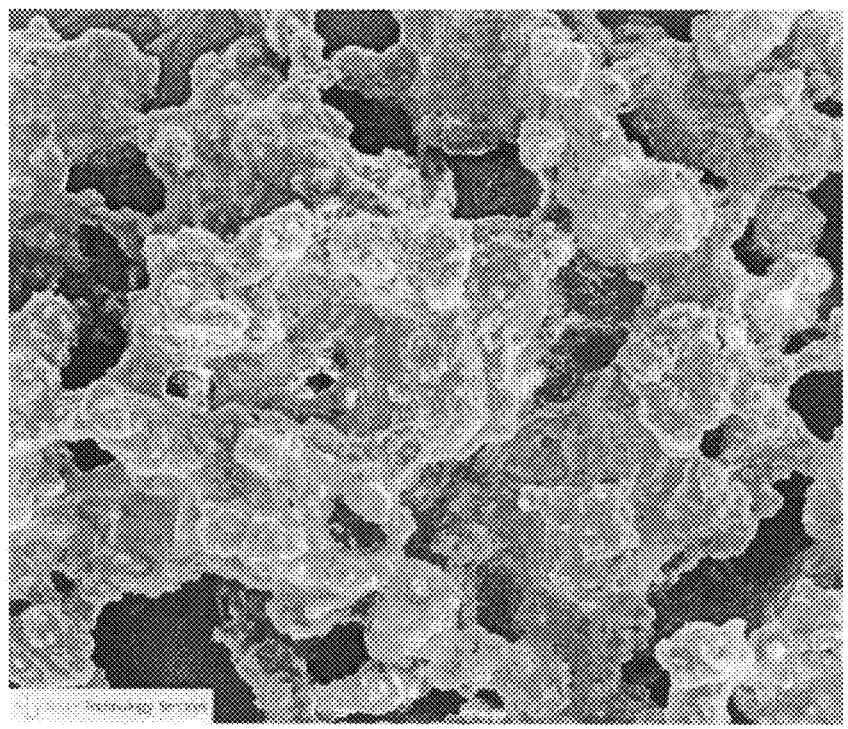
FIG. 2 depicts aspirin particles that have been combined with sodium carbonate in an 80/20 weight ratio and milled for 15 minutes to a reduced particle size in accordance with the invention shown at 200 times magnification.
Figure 3:
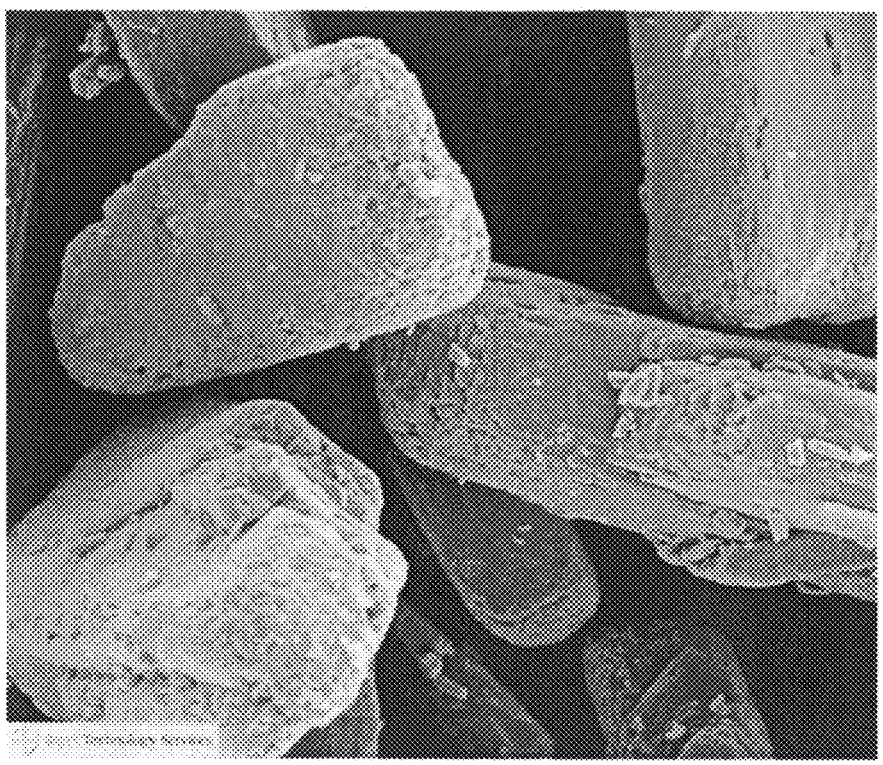
FIG. 3 depicts commercial aspirin particles shown at 200 times magnification.

The effect of the milling time is shown in FIGS. 1, 2, and 3. Unmilled aspirin crystals, magnified 200 times, are shown in FIG. 3. Aspirin crystals milled for fifteen minutes in accordance with the invention, but not combined with a dissolution aid, are shown in FIG. 1, magnified 283 times. It is apparent that the particles in FIG. 1 are substantially smaller than those shown in FIG. 3.

FIG. 2 shows a blend of 80% by weight aspirin crystals and 20% sodium carbonate that has been milled for 15 minutes. When compared to FIG. 1, the coating effect of the sodium carbonate on the aspirin crystals is apparent. Milling should continue until this coating effect is achieved.

After milling, the blend emerges as a powder. If this powder does not have sufficient density, it may be roller compacted to produce granules that improve its density and handling characteristics without damaging the coating effect of the dissolution aid on the medicinal ingredient crystals.

With or without roller compaction, the blend may be compressed into tablets. These tablets may contain commonly known additives, such as diluents, disintegrants, tablet lubricants, binders, glidants, and coloring and flavoring agents. The tablets may further be coated with various materials for reasons known in the art.

One surprising advantage of the invention, however, is that the blend may be advantageously pressed directly into tablets without the addition of additional binders, fillers, or lubricants, thus reducing costs and complexity in handling.

The benefits of the invention are shown more fully in FIGS. 4-7.

FIG. 4 shows a graph of the partial dissolution profile of tablets made in accordance with the invention when compared to a 500 mg aspirin tablet. The data supporting the graph is set forth in Example 8. The tablets prepared with blends had a faster dissolution profile than the plain aspirin tablet. The tablets having 80% by weight aspirin and 20% by weight calcium carbonate and the tablets having 90% by weight aspirin and 10% by weight sodium carbonate, however, were not milled in accordance with the invention. Although these tablets showed marked superiority in speed of dissolution over the plain aspirin tablet, the tablets having 75% by weight aspirin and 25% by weight sodium carbonate that had been milled in accordance with the invention proved to have a the superior dissolution profile. Although the data is not fully shown in FIG. 4, the tablet containing the milled blend of carbonate and aspirin dissolved substantially completely in about two minutes, the unmilled blends were both 98% dissolved in about fifteen minutes, and the plain aspirin did not become 98% dissolved until about twenty-six minutes had passed.

The advantage of the invention is further shown in FIG. 5. The dissolution rates of tablets containing 75% by weight aspirin and 25% by weight sodium carbonate that had been milled for thirty minutes before tabletting and tablets containing 70% by weight aspirin and 30% by weight calcium carbonate milled for fifteen minutes before tabletting were compared to a 500 mg aspirin tablet without any carbonate. The dissolution data for FIG. 5 is set forth in Example 9. As shown in FIG. 5, the milled carbonate blends have superior dissolution rates when compared to the pure aspirin tablet. Although the data is not expressly shown, the aspirin tablet was not 98% dissolved until about twenty-six minutes had passed while tablets made from the milled blends averaged about one minute for the 25% sodium carbonate tablet and about three minutes for the 30% calcium carbonate tablet.

FIG. 6 shows the concentration in blood of aspirin for three formulations of aspirin tablets from animal pK studies. One formulation is a 130 mg aspirin tablet. A second formulation is a micronized aspirin tablet that has been milled to a particle size of d50 ~7 µm before tabletting. A third formulation is a 75% by weight aspirin and 25% by weight sodium carbonate blend that has been milled for five minutes and then formed into a tablet. The data is set forth in Example 10. As shown in the figure, the tablet prepared in accordance with the invention shows a more rapid absorption into the blood stream than either the 130 mg aspirin or micronized aspirin.

FIG. 7 compares the dissolution profiles of several commercial products against a blend of aspirin (85% by weight) and 15% sodium carbonate that has been ball milled for about 5 minutes before tabletting. These formulations contained excipients and did not undergo the roller-compaction. The data supporting FIG. 7 is set forth in Example 11. The tablet made in accordance with the invention has a faster dissolution profile than any of the commercial products. Although the data is not shown in FIG. 7, the 500 mg commercial aspirin tablet was about 95% dissolved after about twenty-six minutes, the commercial naproxen sodium tablet was about 50% dissolved after about twenty-six minutes, the commercial acetaminophen tablet was about 95% dissolved after about nine minutes, the commercial "rapid release" acetaminophen was about 95% dissolved after about seven minutes, the commercial ibuprofen tablet was about 25% dissolved after about twenty-seven minutes, and the commercial ibuprofen liquigel capsule was about 85% dissolved after about twenty-eight minutes.

The manufacturing method in accordance with the invention offers several advantages over conventional processes. By identifying the milling time and ratio of dissolution aid, the process provides a more stable product compared to processes where the medicinally active compound particles are reduced too far or where or milling proceeds for too long, i.e. more than about 30 minutes. Moreover, the cost of production is lower and the final tablet may contain far fewer ingredients and process steps may even be eliminated entirely, which facilitates ease of manufacture.

The tablet itself offers several benefits over conventional tablets. The decrease in particle size following a precise milling time reduces transit time of the active ingredient from GI to bloodstream, thus improving time to onset of action and decreases local GI irritation (due to reduced contact time). The carbonate coating formed as a result of co-milling carbonate with the medicinally active ingredient provides a temporary alkaline barrier between the GI tract and the medicinally active ingredient, which further improves dissolution and reduces GI irritation. The tablet needs to contain only active ingredients allowing for tabletting without the need of additional binders, fillers or disintegrates.

EXAMPLES

Example 1

Selection of Milling Type

Several techniques were evaluated to determine the preferred type of milling techniques for use with aspirin in accordance with the invention. The techniques that were evaluated, and typical particle sizes of particles generated by the technique, are shown in Table 1. All sizes were determined using Laser Diffraction on a model MS 2000 Hydro S machine. The "d50" value is the average particle size of the milled sample, and "d90" represents the average particle size of at least 90% of the particles in the milled sample. Aiijet, bead, and ball mill techniques were selected as being the most preferred in the invention because of the reliability of the techniques and the particle sizes obtained. Bead milling is less preferred because of its higher relative cost. The precipitation method and crystal synthesis also yielded small particle sizes but particles prepared using these techniques tended to agglomerate.

TABLE 1

Milling Techniques and Particle Size

| Milling Technique | Particle size of the milled aspirin |
|---|---|
| High energy Ball Mill | d50 ~30-40 µm |
| Planetary Ball Mill | d50 ~40 µm |
| Air Jet Mill | d50 ~20 µm |
|  | d90 < 10 µm; d50 < 4 µm |
|  | d90 < 6.6 µm; d50 < 2.6 µm using helium as gas jet |
| Bead Mill | d50 < 1.3 µm to <0.8 µm |
| Precipitation Method | d50 ~5 µm |
|  | (Solution: Ethanol + 20% ASA with 10% PVP) |
| Crystal Synthesis | d50 ~5 to 10 µm, with agglomeration of milled particles |
|  | d50 ~30 µm and no agglomeration |

A 75% by weight aspirin and 25% by weight sodium carbonate pre-blend was prepared and portions were subjected to either Ball Mill (ESM) or Air Jet Mill milling techniques to evaluate the effect of the milling techniques on aspirin dissolution times for the blends. The results are shown in Table 2.

TABLE 2

Effect of Milling Techniques on Dissolution Rate

| Mill Type | Milling Time and Percent Aspirin Dissolved | | |
|---|---|---|---|
|  | 2 minutes | 5 minutes | 10 minutes |
| Ball Mill (Model No. ESM) | 95% | 100% | 100% |
| Air Jet Mill | 95% | 96% | 97% |

Example 2

Determination of Compatibility

The degradation products of various combinations of aspirin and various carbonates were determined for different combinations of aspirin and different grades and sources of carbonates to evaluate the compatibility and stability. Milling for about fifteen minutes appeared to slightly induce the production of free salicylic acid (FSA), but not to a significant extent. The percentage of acetyl salicylic salicylic acid (ASSA) was also measured, but it did not demonstrate any significant effects. The results are shown in Table 3 (all blend percentages are weight percentages obtained using High Performance Liquid Chromatography (HPLC))

TABLE 3

Aspirin/Carbonate Blends and Production of Free Salicylic Acid

| Sample Composition | FSA (%) | Acetyl Salicylic Salicylic Acid ASSA (%) |
|---|---|---|
| 100% Aspirin | 0.00 | 0.00 |
| 100% Aspirin-Milled 15 min | 0.00 | 0.00 |
| 80% Aspirin/20% Sodium Carbonate | 0.17 | 0.00 |
| 80% Aspirin/20% Sodium Carbonate-Milled 15 min | 0.36 | 0.00 |
| 75% Aspirin/25% Sodium Carbonate | 0.14 | 0.00 |
| 75% Aspirin/25% Sodium Carbonate-Milled 15 min | 0.22 | 0.00 |
| 70% Aspirin/30% Sodium Carbonate | 0.25 | 0.00 |
| 70% Aspirin/30% Sodium Carbonate-Milled 15 min | 0.33 | 0.00 |
| 64% Aspirin/36% Sodium Carbonate | 0.74 | 0.00 |
| 64% Aspirin/36% Sodium Carbonate-Milled 15 min | 0.84 | 0.00 |
| 78% Aspirin/22% Calcium Carbonate | 0.00 | 0.00 |
| 78% Aspirin/22% Calcium Carbonate-Milled 15 min | 0.17 | 0.00 |
| 70% Aspirin/30% Calcium Carbonate | 0.00 | 0.00 |
| 70% Aspirin/30% Calcium Carbonate-Milled 15 min | 0.12 | 0.00 |
| 75% Aspirin/25% Soda Ash (Dense Density) | 0.23 | 0.01 |
| 75% Aspirin/25% Soda Ash (Dense Density)-Manual Grind | 0.39 | 0.02 |
| 75% Aspirin/25% Calcinated Soda-Milled 15 min | 0.10 | 0.00 |

Example 3

Selection of Aspirin/Carbonate Blends

Various percentages of aspirin and carbonates were prepared, formulated and pressed into pharmaceutical tablets using consistent techniques. The tablets were then tested for aspirin dissolution. The tablets were dissolved in 900 mL of an acetate buffer at pH 4.5 in a Distek OptDiss On-line Detection System. The sample basket was spun at 50 rpm and maintained at 37.0° C., ±0.5°.

The results for tablets with sodium carbonate are shown in Table 4 and the results with calcium carbonate are shown in Table 5. The sample containing 90% aspirin and 10% sodium carbonate exhibited an increased aspirin release profile when compared with samples containing less than 10% sodium carbonate. The samples that contained more than 15% sodium carbonate showed strongly increased dissolution profiles.

TABLE 4

Dissolution Profiles of Aspirin in Various Tablet Formulations

| Sample No. | Weight % Aspirin | Weight % Sodium Carbonate | % ASA Dissolved at: 2 minutes | 5 minutes | 10 minutes |
|---|---|---|---|---|---|
| 1 | 100% | 0% | 11 | 22 | 34 |
| 2 | 95% | 5% | 21 | 35 | 47 |
| 3 | 90% | 10% | 80 | 88 | 93 |
| 4 | 85% | 15% | 97 | 99 | 99 |
| 5 | 80% | 20% | 97 | 99 | 99 |
| 6 | 75% | 25% | 100 | 100 | 101 |

Samples containing 20% or more calcium carbonate also showed marked improved dissolution profiles when compared to samples having less than 20% calcium carbonate.

TABLE 5

Dissolution Profiles of Aspirin in Various Tablet Formulations

| Sample No. | Weight % Aspirin | Weight % Calcium Carbonate | % ASA Dissolved at: 2 minutes | 5 minutes | 10 minutes |
|---|---|---|---|---|---|
| 7 | 100% | 0% | 11 | 22 | 34 |
| 8 | 80% | 20% | 71 | 86 | 93 |
| 9 | 65% | 35% | 79 | 92 | 95 |
| 10 | 55% | 45% | 80 | 96 | 98 |

Example 4

Effect of Milling Times

A blend of 75% by weight aspirin and 25% by weight sodium carbonate was used to evaluate the effect of shorter milling times on aspirin release profiles. The results are shown in Table 6. The milling time for this mixture could be reduced as low as 5 minutes while still demonstrating an enhanced aspirin release profile.

TABLE 6

Aspirin Release Profiles and Milling Time

| | Milling Time (min) | % ASA Dissolved at: 2 minutes | 5 minutes | 10 minutes |
|---|---|---|---|---|
| 75% Aspirin/ | 5 | 97 | 98 | 98 |
| 25% Sodium | 10 | 99 | 99 | 99 |
| Carbonate | 15 | 100 | 100 | 101 |

Example 5

Excipient Effects

A tablet formulated with a binding material (MCC) and a disintegrant (Kollidon CL®) was prepared to evaluate the effect of these materials on the aspirin release profile of a 75 wt % aspirin/25 wt % sodium carbonate blend that was milled for 5 minutes and mixed with the excipients and formed into a tablet. The tablets were dissolved in 900 mL of an acetate buffer at pH 4.5 in a Distek OptDiss On-line Detection System. The sample basket was spun at 50 rpm and maintained at 37.0° C., ±0.5°.

The aspirin release profile of this tablet was compared to the aspirin release profile of tablets made without excipients. There were no significant differences in the aspirin release profiles with or without MCC and/or Kollidon CL®.

Example 6

Roller Compaction

One result of milling the materials in accordance with the invention was that the milled material emerged as a fine, fluffy powder, with a low bulk density. One way to increase the bulk density of powders is through roller compaction, which converts the powder into free flowing granules. To demonstrate that roller compaction did not affect the aspirin release profile of materials prepared in accordance with the invention, samples were prepared using roller compaction and without roller compaction. The results shown in Table 7 confirm that roller compaction did not lower the aspirin release profile.

TABLE 7

Roller Compaction Analysis

| | | % ASA Dissolved at 2/5/10 min | | |
|---|---|---|---|---|
| Formulation | Process | 2 minutes | 5 minutes | 10 minutes |
| 75% Aspirin/ 25% Sodium Carbonate | 5-minute milling | 99 | 100 | 100 |
| | 5-minute milling and then roller compaction | 95 | 100 | 100 |

Example 7

Stability and Packaging

Different types of package materials were evaluated for product stability at accelerated conditions. 75% Aspirin 25% sodium carbonate blends were milled for 15 minutes and stored in powder form in five different package materials: foils with and without desiccant strips, high density polyethylene ("HDPE") bottles with and without desiccant strips, and desiccant tubes. The packaged blends were tested at three different conditions: (a) 25° C. and 60% relative humidity ("RH"), (b) 30° C. and 70% RH, and (c) 40° C. and 75% RH to investigate how the blends degraded. The foil packaging showed favorable stability data, and the added desiccant device significantly improved the product stability. The results are shown in Table 8. "FSA" and "ASSA" have the same meanings as in Table 3.

TABLE 8

Packaging Stability

| Packaging Material | Time (Days) | Storage Condition | FSA (%) | ASSA (%) |
|---|---|---|---|---|
| Foil with Desiccant Strip | 0 | Initial | 0.32 | 0.00 |
| | 77 | 25° C./60% RH | 0.45 | 0.21 |
| | | 30° C./70% RH | 0.61 | 0.38 |
| | | 40° C./75% RH | 0.97 | 1.67 |
| Foil without Desiccant Strip | 0 | Initial | 0.32 | 0.03 |
| | 77 | 25° C./60% RH | 0.46 | 0.12 |
| | | 30° C./70% RH | 0.92 | 0.18 |
| | | 40° C./75% RH | 1.30 | 0.35 |
| HDPE bottle with Desiccant Strip | 0 | Initial | 0.32 | 0.00 |
| | 77 | 25° C./60% RH | 0.81 | 0.24 |
| | | 30° C./70% RH | 1.18 | 0.39 |
| | | 40° C./75% RH | >3.0 | n/a |
| HDPE bottle without Desiccant Strip | 0 | Initial | 0.32 | 0.00 |
| | 77 | 25° C./60% RH | 1.96 | 0.19 |
| | | 30° C./70% RH | 3.63 | 0.29 |
| | | 40° C./75% RH | >3.0 | n/a |
| Desiccant Tube | 0 | Initial | 0.32 | 0.00 |
| | 77 | 25° C./60% RH | 1.02 | 0.26 |
| | | 30° C./70% RH | 1.01 | 0.53 |
| | | 40° C./75% RH | 2.60 | 1.35 |

To investigate the stability of compressed tablets made in accordance with the invention, aspirin/sodium carbonate (75%/25%) blends were milled for 5 minutes; roller compacted and pressed into tablets. The tablets were stored in six different packaging materials at three different conditions: (a) 25° C. and 60% RH, 30° C. and 70% RH, and 40° C. and 75% to investigate how the tablets degraded. The ascending order of free salicylic acid ("FSA") was found to be: Desiccant Coated Foil<Desiccant Coated Tube<HDPE Bottle with Desiccant Canister<Blister COC<Blister ACLAR<Blister PP. "FSA" and "ASSA" have the same meanings as in Table 3

TABLE 9

Packaging and Tablets

| Packaging Material | Time (Days) | Storage Condition | FSA (%) | ASSA (%) |
|---|---|---|---|---|
| Desiccant Coated Foil | 0 | Initial | 0.66 | 0.03 |
| | 31 | 25° C./60% RH | 0.54 | 0.12 |
| | | 30° C./70% RH | 0.58 | 0.21 |
| | | 40° C./75% RH | 0.70 | 0.76 |
| Desiccant Coated Tube | 0 | Initial | 0.66 | 0.03 |
| | 31 | 25° C./60% RH | 0.56 | 0.14 |
| | | 30° C./70% RH | 0.56 | 0.25 |
| | | 40° C./75% RH | 0.73 | 0.85 |
| HDPE Bottle with Desiccant Canister | 0 | Initial | 0.66 | 0.03 |
| | 31 | 25° C./60% RH | 0.56 | 0.14 |
| | | 30° C./70% RH | 0.57 | 0.23 |
| | | 40° C./75% RH | 1.18 | 0.78 |
| Blister COC (tri-layer of 30 μm polypropylene/ 300 μm COC/30 μm polypropylene) (supplied by Kloeckner) | 0 | Initial | 0.66 | 0.03 |
| | 24 | 25° C./60% RH | 1.31 | 0.15 |
| | | 30° C./70% RH | 2.21 | 0.30 |
| | | 40° C./75% RH | >3.0 | n/a |
| Blister PP (300 μm polypropylene monolayer) (supplier Tekni-Films) | 0 | Initial | 0.66 | 0.03 |
| | 24 | 25° C./60% RH | 1.87 | 0.20 |
| | | 30° C./70% RH | 3.94 | 0.44 |
| | | 40° C./75% RH | >3.0 | n/a |
| Blister Aclar (tri-layer of 250 μm polyvinyl chloride/ 50 μm polyethylene/ 15 μm Aclar) (supplier Kloeckner) | 0 | Initial | 0.66 | 0.03 |
| | 24 | 25° C./60% RH | 1.38 | 0.15 |
| | | 30° C./70% RH | 2.61 | 0.33 |
| | | 40° C./75% RH | >3.0 | n/a |

Example 8

Tablets were prepared comprising: excipients and (a) a mixture of 75% by weight aspirin and 25% by weight sodium carbonate that had been milled for 15 minutes; (b) a mixture of 90% by weight aspirin and 10% by weight sodium carbonate that had not been milled; or (c) a mixture of 80% by weight aspirin and 20% by weight calcium carbonate that had not been milled. The tablets were compressed at 10 kilonewtons. The dissolution rates of these tablets were compared to the dissolution rate of a 500 mg aspirin tablet. The dissolution tests were carried out as in the previous examples. The results for the first five minutes of the dissolution test are set out in Table 10, and the average of the two tablets results are shown in FIG. 4. Although the dissolution tests were carried out for thirty minutes, only the first five minutes of the test are shown to highlight the differences in the tablet dissolution profiles.

TABLE 10

Comparison of milling

| Time (min:sec) | 75% aspirin 25% sodium carbonate (15 minutes milled) | | 90% aspirin 10% sodium carbonate (not milled) | | 80% aspirin 20% calcium carbonate (not milled) | | 500 mg aspirin tablet | |
|---|---|---|---|---|---|---|---|---|
| | Tablet 1 Percent Dissolved | Tablet 2 Percent Dissolved | Tablet 1 Percent Dissolved | Tablet 2 Percent Dissolved | Tablet 1 Percent Dissolved | Tablet 2 Percent Dissolved | Tablet 1 Percent Dissolved | Tablet 2 Percent Dissolved |
| 0:00 | 0.1 | 0.2 | 0.2 | 0.0 | −0.6 | −0.3 | −0.3 | 0.3 |
| 0:10 | 8.3 | 19.1 | 12.1 | 13.3 | 7.9 | 3.2 | 0.0 | 0.3 |
| 0:20 | 26.9 | 26.2 | 25.9 | 29.9 | 11.8 | 17.2 | 0.2 | 0.4 |
| 0:30 | 60.3 | 41.9 | 35.7 | 32.0 | 32.4 | 40.5 | 0.2 | 1.2 |
| 0:40 | 72.8 | 66.3 | 47.2 | 46.1 | 36.6 | 44.6 | 1.9 | 1.8 |
| 0:50 | 76.2 | 63.8 | 59.1 | 48.5 | 48.3 | 49.3 | 6.3 | 3.9 |
| 1:00 | 89.8 | 87.8 | 63.0 | 64.0 | 48.9 | 60.0 | 3.6 | 3.3 |
| 1:50 | 100.8 | 100.6 | 68.8 | 68.1 | 69.3 | 68.9 | 6.4 | 6.6 |
| 2:20 | 100.4 | 100.2 | 71.0 | 71.9 | 74.4 | 72.8 | 7.4 | 7.2 |
| 2:30 | 100.6 | 99.8 | 70.9 | 72.0 | 75.8 | 72.8 | 11.3 | 11.6 |
| 2:40 | 100.1 | 99.8 | 72.3 | 73.3 | 76.8 | 74.6 | 10.8 | 11.6 |
| 2:50 | 99.9 | 99.6 | 73.7 | 73.5 | 76.8 | 75.3 | 11.6 | 11.5 |
| 3:00 | 100.1 | 99.5 | 74.8 | 75.2 | 79.3 | 77.9 | 13.5 | 13.4 |
| 3:10 | 100.2 | 99.7 | 76.1 | 75.4 | 78.8 | 78.4 | 14.1 | 14.4 |
| 3:20 | 99.8 | 100.0 | 76.8 | 77.2 | 80.2 | 78.4 | 15.3 | 14.1 |
| 3:30 | 100.3 | 99.6 | 76.7 | 78.7 | 82.2 | 79.7 | 16.0 | 15.7 |
| 3:40 | 100.1 | 99.9 | 78.8 | 78.6 | 82.1 | 81.1 | 17.9 | 16.0 |
| 3:50 | 100.2 | 100.3 | 78.4 | 79.6 | 82.0 | 81.7 | 17.9 | 16.7 |
| 4:00 | 100.4 | 99.9 | 78.1 | 80.3 | 83.2 | 83.8 | 18.0 | 17.3 |
| 4:10 | 100.4 | 100.2 | 80.5 | 81.0 | 83.7 | 83.5 | 21.7 | 21.0 |
| 4:20 | 100.4 | 100.4 | 81.4 | 81.4 | 85.1 | 83.8 | 20.0 | 20.4 |
| 4:30 | 100.3 | 100.2 | 81.8 | 81.7 | 85.7 | 83.6 | 22.0 | 19.6 |
| 4:40 | 99.6 | 100.2 | 82.5 | 83.7 | 86.0 | 85.0 | 22.5 | 21.6 |
| 4:50 | 99.8 | 100.1 | 82.1 | 83.5 | 85.8 | 85.2 | 23.1 | 22.8 |
| 5:00 | 100.3 | 100.0 | 82.8 | 84.1 | 86.2 | 85.9 | 25.3 | 21.2 |

Example 9

Tablets were prepared comprising: excipients and (a) a mixture of 75% by weight aspirin and 25% by weight sodium carbonate that had been milled for 30 minutes; (b) a mixture of 70% by weight aspirin and 30% by weight calcium carbonate that had been milled for 15 minutes and. The tablets were compressed at 10 kilonewtons. The dissolution rates of these tablets were compared to the dissolution rate of a 500 mg aspirin tablet. The dissolution tests were carried out as in the previous examples. The results for the first five minutes of the dissolution test are set out in Table 11, and the average of the two tablets results are shown in FIG. 4 for each blend. Although the dissolution tests were carried out for thirty minutes, only the first five minutes of the test are shown to highlight the differences in the tablet dissolution profiles.

TABLE 11

Comparison of Various Blends

| Time (min:sec) | 75% aspirin 25% sodium carbonate (30 minutes milled) | | 70% aspirin 30% calcium carbonate (15 minutes milled) | | 500 Mg aspirin tablet | |
|---|---|---|---|---|---|---|
| | Tablet 1 Percent Dissolved | Tablet 2 Percent Dissolved | Tablet 1 Percent Dissolved | Tablet 2 Percent Dissolved | Tablet 1 Percent Dissolved | Tablet 2 Percent Dissolved |
| 0:00 | 0.2 | 0.2 | 0.9 | 0.2 | −0.3 | 0.3 |
| 0:10 | 12.5 | 9.1 | 7.5 | −0.1 | 0.0 | 0.3 |
| 0:20 | 60.7 | 53.2 | 8.8 | 12.9 | 0.2 | 0.4 |
| 0:30 | 85.7 | 85.0 | 22.5 | 18.6 | 0.2 | 1.2 |
| 0:40 | 96.1 | 98.2 | 41.2 | 27.6 | 1.2 | 1.5 |
| 0:50 | 102.0 | 94.5 | 38.7 | 30.3 | 1.9 | 1.8 |
| 1:00 | 102.7 | 100.5 | 58.3 | 46.5 | 6.3 | 3.9 |
| 1:10 | 100.7 | 100.4 | 67.8 | 46.2 | 3.6 | 3.3 |
| 1:20 | 100.8 | 100.3 | 74.3 | 50.6 | 3.9 | 4.6 |
| 1:30 | 101.5 | 100.9 | 78.1 | 59.3 | 5.4 | 5.1 |
| 1:40 | 102.4 | 101.3 | 87.3 | 69.0 | 5.9 | 4.7 |
| 1:50 | 101.6 | 101.5 | 86.3 | 72.7 | 6.4 | 6.6 |
| 2:00 | 102.2 | 100.9 | 90.1 | 75.2 | 7.4 | 7.2 |
| 2:10 | 102.6 | 100.7 | 95.5 | 77.7 | 8.4 | 7.8 |
| 2:20 | 102.4 | 101.1 | 96.9 | 80.2 | 10.4 | 10.9 |
| 2:30 | 102.4 | 101.2 | 96.9 | 93.1 | 11.3 | 11.6 |
| 2:40 | 102.3 | 101.6 | 97.1 | 93.1 | 10.8 | 11.6 |
| 2:50 | 102.5 | 101.4 | 97.1 | 98.2 | 11.6 | 11.5 |
| 3:00 | 102.8 | 101.4 | 97.7 | 99.0 | 13.5 | 13.4 |
| 3:10 | 102.6 | 101.5 | 97.9 | 100.7 | 14.1 | 14.4 |
| 3:20 | 102.5 | 101.3 | 97.7 | 101.7 | 15.3 | 14.1 |
| 3:30 | 102.4 | 101.3 | 97.4 | 101.0 | 16.0 | 15.7 |
| 3:40 | 102.9 | 101.2 | 97.5 | 101.7 | 17.9 | 16.0 |
| 3:50 | 102.6 | 101.0 | 97.4 | 101.2 | 17.9 | 16.7 |
| 4:00 | 102.5 | 101.3 | 97.3 | 101.3 | 18.0 | 17.3 |
| 4:10 | 102.5 | 101.5 | 97.4 | 101.1 | 21.7 | 21.0 |
| 4:20 | 102.7 | 101.2 | 97.1 | 101.3 | 20.0 | 20.4 |
| 4:30 | 102.6 | 101.6 | 97.2 | 101.2 | 22.0 | 19.6 |
| 4:40 | 102.6 | 101.8 | 97.5 | 101.0 | 22.5 | 21.6 |
| 4:50 | 102.4 | 101.4 | 97.1 | 101.0 | 23.1 | 22.8 |
| 5:00 | 102.5 | 101.8 | 97.4 | 101.2 | 25.3 | 21.2 |

Example 10

Doses of a commercial aspirin product, an aspirin product micronized by air jet milling and a blend of 75% by weight aspirin and 25% by weight sodium carbonate that had been ball milled for five minutes and formed into a tablet were fed to five dogs each, and blood samples were taken from the dogs at intervals and the pK of the samples were measured to determine the rate of absorption of thee aspirin. Because in vivo studies tend to have variable results, the values were averaged, and the results calculated are shown in FIG. 6 and in Table 12. The micronized and ball milled samples showed substantially faster absorption profiles than did the commercial product.

TABLE 12

Average PK Values for Aspirin Formulations

| Time (min) | Micronized via Air Jet Mill | Marketed aspirin | 75% aspirin, 25% sodium carbonate, ball-milled 5 min |
|---|---|---|---|
| 0 | 0.00 | 0.48 | 1.09 |
| 2 | 11.49 | 0.31 | 9.11 |
| 5 | 646.93 | 59.46 | 1,071.20 |
| 8 | 2,282.43 | 104.52 | 3,724.80 |
| 10 | 2,750.56 | 154.48 | 4,232.00 |

TABLE 12-continued

Average PK Values for Aspirin Formulations

| Time (min) | Micronized via Air Jet Mill | Marketed aspirin | 75% aspirin, 25% sodium carbonate, ball-milled 5 min |
|---|---|---|---|
| 13 | 3,447.29 | 256.60 | 4,896.00 |
| 15 | 4,304.79 | 243.93 | 4,984.00 |
| 30 | 3,543.40 | 974.02 | 3,428.00 |
| 45 | 2,243.60 | 2,313.08 | 2,214.60 |
| 60 | 1,332.00 | 2,592.14 | 745.80 |
| 120 | 30.45 | 407.48 | 43.70 |

Example 11

Commercial samples were purchased and subjected to dissolution tests in the same manner as set forth in the previous examples. A 500 mg aspirin tablet was prepared in accordance with the invention containing a blend of 85% by weight aspirin and 15% by weight sodium carbonate that had been ball milled for about 5 minutes. The results are set forth in Table 13.

TABLE 13

Comparison of Dissolution Rates of Commercial Products

| | Percent Dissolved | | | | | | |
|---|---|---|---|---|---|---|---|
| Time (min:sec) | 500 mg Bayer aspirin | 220 mg Aleve naproxen sodium | 500 mg Tylenol acetaminophen | 500 mg Tylenol Rapid Release acetaminophen | 200 mg Advil ibuprofen | 200 mg Advil LiquiGel ibuprofen | Invention |
| 0:00 | 0.3 | 0.5 | 0.0 | 0.0 | −0.2 | 0.0 | 0.6 |
| 0:10 | 0.0 | 0.6 | 0.0 | 0.0 | 0.2 | 0.0 | 5.0 |
| 0:20 | 0.1 | 0.2 | 0.0 | 0.0 | −0.2 | 0.0 | 7.7 |
| 0:30 | 0.2 | −0.6 | 0.8 | 0.9 | 0.0 | −0.1 | 17.5 |
| 0:40 | 0.4 | −0.2 | 1.0 | 0.7 | −0.1 | 0.0 | 25.9 |
| 0:50 | 0.2 | 0.3 | 3.1 | 1.4 | 0.0 | 0.0 | 32.7 |
| 1:00 | 1.1 | −0.6 | 12.8 | 6.5 | −0.3 | 0.0 | 34.6 |
| 1:10 | 2.0 | 0.2 | 17.3 | 6.9 | 0.2 | 0.0 | 46.3 |
| 1:20 | 2.4 | −0.1 | 17.8 | 17.0 | −0.1 | 0.1 | 54.2 |
| 1:30 | 3.5 | 0.4 | 18.8 | 18.0 | 0.1 | 0.1 | 66.0 |
| 1:40 | 4.5 | 0.9 | 30.5 | 27.2 | 0.3 | 0.1 | 64.9 |
| 1:50 | 3.6 | 0.2 | 37.9 | 38.4 | 0.2 | 0.1 | 70.4 |
| 2:00 | 4.8 | 1.0 | 39.0 | 37.9 | 0.1 | 0.3 | 78.8 |
| 2:10 | 5.5 | 1.6 | 43.3 | 55.1 | 0.1 | 0.3 | 86.0 |
| 2:20 | 7.2 | 1.8 | 48.7 | 42.4 | 0.3 | 0.2 | 88.9 |
| 2:30 | 7.9 | 1.7 | 50.6 | 49.2 | 0.0 | 0.4 | 93.3 |
| 2:40 | 10.3 | 1.0 | 55.5 | 53.0 | 0.1 | 0.4 | 96.7 |
| 2:50 | 11.1 | 1.3 | 52.2 | 55.0 | −0.1 | 0.6 | 96.8 |
| 3:00 | 10.3 | 2.6 | 53.4 | 57.7 | 0.2 | 0.6 | 97.2 |
| 3:10 | 10.2 | 2.2 | 58.6 | 61.3 | 0.0 | 0.7 | 97.5 |
| 3:20 | 12.6 | 1.9 | 60.7 | 65.1 | 0.0 | 1.0 | 97.0 |
| 3:30 | 13.1 | 2.1 | 70.4 | 64.4 | 0.1 | 1.1 | 97.6 |
| 3:40 | 11.8 | 3.2 | 66.7 | 68.8 | −0.1 | 1.1 | 98.0 |
| 3:50 | 12.4 | 3.0 | 69.5 | 69.9 | −0.1 | 1.4 | 97.3 |
| 4:00 | 15.8 | 2.9 | 72.4 | 76.3 | 0.0 | 1.5 | 98.2 |
| 4:10 | 15.1 | 2.9 | 72.9 | 74.0 | −0.2 | 1.5 | 98.4 |
| 4:20 | 16.0 | 3.8 | 74.2 | 78.5 | −0.1 | 1.6 | 97.7 |
| 4:30 | 16.8 | 4.2 | 79.8 | 79.8 | 0.0 | 1.8 | 98.4 |
| 4:40 | 18.4 | 3.4 | 81.9 | 81.7 | 0.1 | 1.9 | 98.6 |
| 4:50 | 17.7 | 6.5 | 83.0 | 81.5 | 0.0 | 2.0 | 98.1 |
| 5:00 | 19.9 | 3.4 | 84.0 | 85.8 | −0.1 | 1.9 | 98.6 |

The purpose of the above description is to illustrate some embodiments of the present invention without implying a limitation. It will apparent to those skilled in the art that various modifications and variations may be made in the apparatus or procedure of the invention without departing from the scope or spirit of the invention.

What is claimed is:

1. A compressed tablet for oral administration consisting essentially of:
   a. acetylsalicylic acid, and
   b. sodium carbonate,
the acetylsalicylic acid having a d50 particle size prior to tableting of less than about 40 microns measured by wet dispersion laser diffraction, and wherein the weight ratio of acetylsalicylic acid to sodium carbonate is about 3:1, the tablet being 100% dissolvable after 2 minutes in 900 L of an acetate buffer at pH 4.5 in a dissolution testing system in which a sample basket is spun at 50 rpm and maintained at about 37° C.

2. A compressed tablet for oral administration consisting of:
   a. acetylsalicylic acid, and
   b. sodium carbonate,
the acetylsalicylic acid having a d50 particle size prior to tableting of less than about 40 microns measured by wet dispersion laser diffraction, and wherein the weight ratio of acetylsalicylic acid to sodium carbonate is about 3:1, the tablet being 100% dissolvable after 2 minutes in 900 L of an acetate buffer at pH 4.5 in a dissolution testing system in which a sample basket is spun at 50 rpm and maintained at about 37° C.

3. A compressed tablet for oral administration adapted to achieve in a dog an average plasma concentration of about 1071 ng of aspirin per milliliter of plasma at 5 minutes after administration thereof, the compressed tablet consisting essentially of: acetylsalicylic acid and sodium carbonate, the acetylsalicylic acid having an average particle size prior to tableting of less than about 40 microns measured by wet dispersion laser diffraction, and wherein the weight ratio of acetylsalicylic acid to sodium carbonate is about 3:1, the tablet being 100% dissolvable after 2 minutes in 900 mL of an acetate buffer at pH 4.5 in a dissolution testing system in which a sample basket is spun at 50 rpm and maintained at about 37° C.

* * * * *